US012797104B2

(12) United States Patent
Akbarian et al.

(10) Patent No.: US 12,797,104 B2
(45) Date of Patent: Nov. 17, 2026

(54) BI-DIRECTIONAL ARTICULATING SURGICAL SHAVER

(71) Applicant: Acclarent, Inc., Irvine, CA (US)

(72) Inventors: Fatemeh Akbarian, Rancho Palos Verdes, CA (US); Itzhak Fang, Irvine, CA (US); Jetmir Palushi, Irvine, CA (US); Henry F. Salazar, Pico Rivera, CA (US)

(73) Assignee: Acclarent, Inc., Irvine, CA (US)

( * ) Notice: Subject to any disclaimer, the term of this patent is extended or adjusted under 35 U.S.C. 154(b) by 382 days.

(21) Appl. No.: 18/218,712

(22) Filed: Jul. 6, 2023

(65) Prior Publication Data

US 2023/0355264 A1 Nov. 9, 2023

Related U.S. Application Data

(63) Continuation of application No. 16/666,484, filed on Oct. 29, 2019, now abandoned.

(Continued)

(51) Int. Cl.

*A61B 17/32* (2006.01)
*A61B 17/24* (2006.01)
*A61B 17/00* (2006.01)

(52) U.S. Cl.

CPC ........ *A61B 17/32002* (2013.01); *A61B 17/24* (2013.01); *A61B 2017/00318* (2013.01);

(Continued)

(58) Field of Classification Search

CPC .... A61B 17/32002; A61B 2017/00318; A61B 2017/320032; A61B 2017/32008; A61B 17/24; A61B 2017/320024

See application file for complete search history.

(56) References Cited

U.S. PATENT DOCUMENTS 4,646,738 A * 3/1987 Trott ................ A61B 17/32002 604/266
5,437,630 A * 8/1995 Daniel ............. A61B 17/32002 606/180

(Continued)

FOREIGN PATENT DOCUMENTS

JP H01-119241 A 5/1989
JP H06-269459 A 9/1994

(Continued)

OTHER PUBLICATIONS

International Search Report and Written Opinion dated Feb. 12, 2020 for International Application No. PCT/IB2019/060238, 13 pages.

(Continued)

*Primary Examiner* — Christina C Lauer
(74) *Attorney, Agent, or Firm* — Morgan, Lewis & Bockius LLP

(57) ABSTRACT

A surgical instrument for cutting a tissue and related methods includes a shaft, a cutting member, and an axial adjustment coupling. The shaft and the cutting member are configured to articulate from a first configuration toward a second configuration and respectively have distal and proximal shaft ends distal and proximal member ends. The cutting member is disposed within the shaft and configured to cyclically move relative to the shaft. The axial adjustment coupling is configured to longitudinally move the proximal member end relative to the proximal shaft end while articulating the shaft and the cutting member from the first configuration toward the second configuration. Thereby, the axial adjustment coupling inhibits movement of the distal member end relative to the distal shaft end for maintaining alignment between a shaft window opening in the shaft and a cutting window opening in the cutting member.

20 Claims, 5 Drawing Sheets

Related U.S. Application Data

(60) Provisional application No. 62/775,135, filed on Dec. 4, 2018.

(52) U.S. Cl.
CPC ............... *A61B 2017/00323* (2013.01); *A61B 2217/005* (2013.01)

(56) References Cited

U.S. PATENT DOCUMENTS

| | | | | | |
|---|---|---|---|---|---|
| 5,462,527 | A | * | 10/1995 | Stevens-Wright | A61M 25/0147 604/95.04 |
| 5,620,447 | A | * | 4/1997 | Smith | A61B 17/32002 606/180 |
| 5,669,926 | A | * | 9/1997 | Aust | A61B 17/32002 606/180 |
| 5,707,350 | A | | 1/1998 | Krause et al. | |
| 5,794,626 | A | * | 8/1998 | Kieturakis | A61B 90/10 600/567 |
| 7,720,521 | B2 | | 5/2010 | Chang et al. | |
| 8,123,722 | B2 | | 2/2012 | Chang et al. | |
| 8,190,389 | B2 | | 5/2012 | Kim et al. | |
| 8,320,711 | B2 | | 11/2012 | Altmann et al. | |
| 8,702,626 | B1 | | 4/2014 | Kim et al. | |
| 9,167,961 | B2 | | 10/2015 | Makower et al. | |
| 9,198,736 | B2 | | 12/2015 | Kim et al. | |
| 10,631,890 | B2 | | 4/2020 | Palushi et al. | |
| 2007/0208252 | A1 | | 9/2007 | Makower | |
| 2011/0060214 | A1 | | 3/2011 | Makower | |
| 2014/0148729 | A1 | | 5/2014 | Schmitz et al. | |
| 2014/0200444 | A1 | | 7/2014 | Kim et al. | |
| 2014/0364725 | A1 | | 12/2014 | Makower | |
| 2015/0150580 | A1 | * | 6/2015 | Dubois | A61B 17/32 606/49 |
| 2015/0374401 | A1 | | 12/2015 | Guggenheimer et al. | |
| 2016/0008083 | A1 | | 1/2016 | Kesten et al. | |
| 2016/0066943 | A1 | | 3/2016 | Oliver et al. | |
| 2016/0310042 | A1 | | 10/2016 | Kesten et al. | |
| 2018/0000499 | A1 | * | 1/2018 | Altman | A61B 17/24 |
| 2018/0242962 | A1 | | 8/2018 | Walen et al. | |
| 2020/0170659 | A1 | | 6/2020 | Akbarian et al. | |

FOREIGN PATENT DOCUMENTS

| | | | |
|---|---|---|---|
| JP | H06-292728 | A | 10/1994 |
| JP | H09-084878 | A | 3/1997 |
| JP | H10-005235 | A | 1/1998 |

OTHER PUBLICATIONS

Japanese Office Action, Notice of Reasons for Refusal, and Search Report by Registered Search Organization, dated Aug. 8, 2023 for Application No. JP 2021-531740, 21 pgs.

U.S. Appl. No. 62/555,824, entitled "Apparatus to Secure Field Generating Device to Chair," filed Sep. 8, 2017.

* cited by examiner

BI-DIRECTIONAL ARTICULATING SURGICAL SHAVER

PRIORITY

This application is a continuation of U.S. application Ser. No. 16/666,484, filed Oct. 29, 2019, published as U.S. Pub. No. 2022/0170659. U.S. Application Ser. No. 16/666,484 claims priority to U.S. Provisional Pat. App. No. 62/775,135, entitled "Bi-Directional Articulating Surgical Shaver," filed Dec. 4, 2018, the disclosure of which is incorporated by reference herein.

BACKGROUND

Surgical cutting instruments configured for removal of lesions, polyps and fibroids within the nasal cavity are known. Some configurations may include an elongated inner member rotatably coaxially disposed within a tubular outer member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue, such as bone tissue, to be done, with the opening configured to cooperate with the specific cutting edge configuration.

To use such surgical cutting instrument to address such tissues, the opening/cutting edge is advanced to the target surgical site, and the opening positioned adjacent the tissue to be removed. The opening may be repositioned to address tissue which could not be accessed with the instrument in the previous position. Surgical cutting instruments with a fixed opening allow surgeons to cut only in the direction of the fixed opening cutting. To access, cut and remove tissue at various locations, surgeons have to reposition the instrument at various angles; or in some instances, change to other instruments having a more appropriately arranged opening.

It may be desirable to access, cut and remove tissue, such as bone tissue, at various locations without having to reposition or change the surgical instrument. While several different surgical instruments and methods of use have been made for tissue removal within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
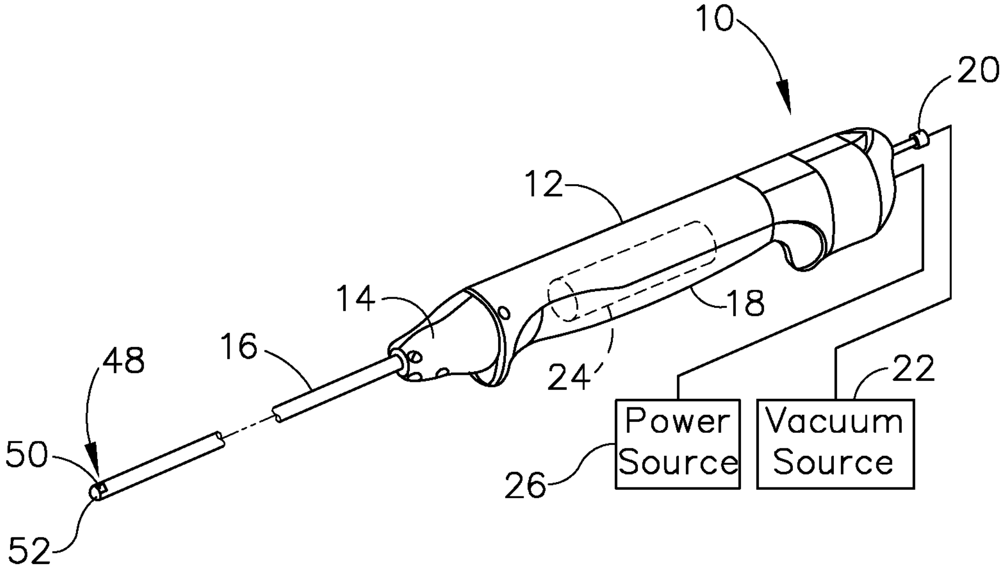
FIG. 1 depicts a perspective view of a first exemplary surgical cutting instrument having a handle assembly and a shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "upward," "downward," "side," "axial," and "longitudinal" also are used herein for reference to relative positions and directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY SURGICAL CUTTING INSTRUMENT

Figure 2:
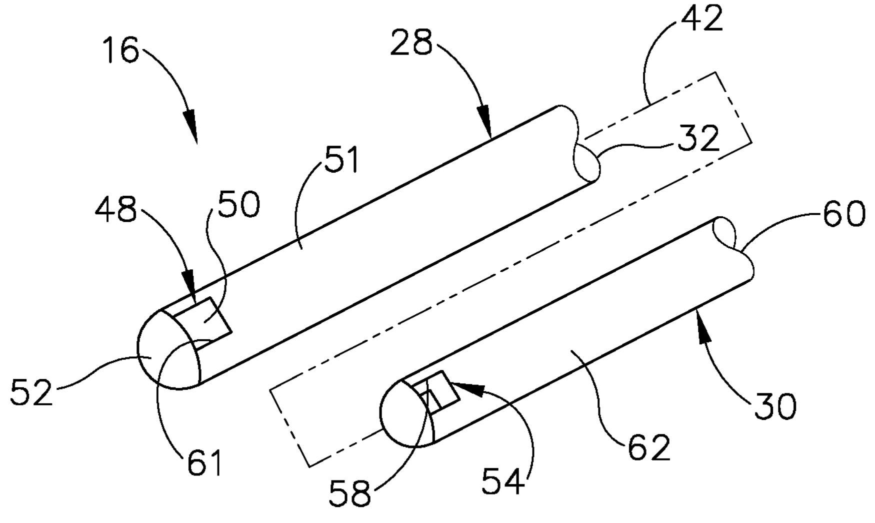
FIG. 2 depicts an exploded perspective fragmentary view of the shaft assembly of FIG. 1 having a shaft and a cutting member.

FIG. 1-2 show a first exemplary surgical cutting instrument (10) that may be used to remove tissue, such as bone tissue, from the nasal cavity, as well as from any other suitable location. Surgical cutting instrument (10) of the present example includes a handle assembly (12), a hub (14), and a shaft assembly (16) extending distally from handle assembly (12). Handle assembly (12) has a handle (18) which may be of any suitable configuration. Handle (18) may include controls for the operation of surgical cutting instrument (10), or the controls may be located remotely. Surgical cutting instrument (10) further includes a suction port (20) operatively connected to a vacuum source (22) and configured to enable aspiration of tissue, such as a bone tissue, from a surgical site. Rotational motion is delivered by a motorized drive assembly (24) within handle assembly (12) to shaft assembly (16) in the present example, although any suitable rotational or oscillatory motion source may be utilized. For example, such motion source may be housed within handle assembly (12) or may be external and connectable to handle assembly (12). A power source (26) connects to motorized drive assembly (24) to power surgical cutting instrument (10) for use. In addition or alternatively, handle assembly (12) may house a battery (not shown).

Shaft assembly (16) generally includes an outer shaft (28) and an inner cutting member (30) collectively configured to receive and remove tissue from the surgical site. Cutting member (30), which is illustrated as a tube, is disposed within a longitudinally extending lumen (32) of shaft (28). Cutting member (30) is configured to be rotated about a longitudinal axis (42) of shaft assembly (16) at a distal portion. Although shaft assembly (16) is depicted as rigid, all or a portion of shaft assembly (16) may be flexible, with longitudinal axis (42) comprising a series of cross-sectional centers. Cutting member (30) defines a lumen and extends proximally to handle assembly (12) and connects to motorized drive assembly (24), which rotatably drives cutting member (30) relative to shaft (28). In the present example, shaft (28) is formed of polycarbonate and cutting member (30) is formed of stainless steel. Of course, shaft (28) and cutting member (30) may be formed of one or more alternative materials in accordance with the invention described herein. The invention is thus not intended to be unnecessarily limited to manufacture with polycarbonate and stainless steel. While the present example of cutting member (30) is a hollow tube, cutting member (30) is not limited to being tubular and defining its own lumen (32).

Shaft (28) includes a window region (48) having a shaft opening, such as a shaft window opening (50), at a distal portion thereof. Distal portion includes a tubular sidewall (51) that distally terminates in a curved end, such as a generally hemispherical end (52). Shaft window opening (50) extends through tubular sidewall (51) of shaft (28) into lumen (32) and is in fluid communication with the environment surrounding shaft (28). Shaft window opening (50) faces radially outward relative to longitudinal axis (42) such that tissue is configured to be radially received through shaft window opening (50) into a central suction lumen (60) of cutting member (30) in a radially inward direction. Shaft window opening (50) is surrounded by a relatively dull edge (61).

Cutting member (30) includes a cutting window opening (54) at distal portion of cutting member (30). Cutting window opening (54) is configured to longitudinally align with shaft window opening (50) and includes a cutting edge (58) extending therealong. It is noted that less than the entirety of cutting edge (58) may be configured for cutting tissue against an opposing edge (61) of shaft (28). At least a portion of cutting edge (58) is disposed to move adjacent to and across at least a portion of window region (48) when cutting member (30) is rotated or oscillated about longitudinal axis (42). By way of example, as cutting member (30) moves in a clockwise direction, edge (61) of window region (48) provides an opposing surface to cutting edge (58) whereby tissue may be severed to remove a cut tissue portion therefrom. Cutting edge (58) and edge (61) may have any configuration which suitably cooperates with the other to sever tissue, such as a knife edge, a serrated edge, bipolar, monopolar or harmonic energy modality, or laser activated cutting edge.

The extent of movement and position of cutting edge (58) relative to edge (61) is sufficient to separate tissue, whether by severing, tearing or any other mechanism. For example, cutting edge (58) may cyclically move across at least a portion of window region (48). Further clockwise movement of cutting member (30) will advance cutting edge (58) past edge (61), such as results from oscillation about longitudinal axis (42) or from full rotation about longitudinal axis (42).

With continued reference to FIGS. 1-2, vacuum source (22) generates suction in a proximal direction along suction lumen (60) and longitudinal axis (42) toward suction port (20). Suction lumen (60) is defined by a tubular sidewall (62) of cutting member (30) in the present example and is in direct fluid communication with cutting window opening (54). Without tissue blocking cutting window opening (54), such suction proximally withdraws a window airflow therethrough along suction lumen (60). However, once tissue is respectively introduced into window opening (54), suction effectively draws tissue into window opening (54) for resection while tissue blocks airflow along suction lumen (60). Airflow through suction lumen (60) essentially terminates such that vacuum source (22) accumulates the vacuum within suction lumen (60). Such termination of airflow may generally be referred to as a stalled airflow within lumen. Additional details regarding airflow through lumen and aspiration vents for improving such airflow are discussed in alternative examples described in U.S. patent application Ser. No. 15/795,473, entitled "Tissue Shaving Instrument," filed Oct. 27, 2017, the disclosure of which is incorporated by reference herein.

Furthermore, surgical cutting instrument (10) may be used in conjunction with an image-guide surgery (IGS) navigation system, medical procedure chair, and displays described alone or in any combination according to the following: U.S. Pat. Pub. No. 2016/0008083, entitled "Guidewire Navigation for Sinuplasty," published Jan. 14, 2016; U.S. Patent App. No. 62/555,824, entitled "Apparatus to Secure Field Generating Device to Chair," filed Sep. 8, 2017; U.S. Pat. Pub. No. 2016/0008083, entitled "Guidewire Navigation for Sinuplasty," published Jan. 14, 2016; U.S.

Pat. Pub. No. 2016/0310042, entitled "System and Method to Map Structures of Nasal Cavity," published Oct. 27, 2016; U.S. Pat. No. 8,702,626, entitled "Guidewires for Performing Image Guided Procedures," issued Apr. 22, 2014; U.S. Pat. No. 8,320,711, entitled "Anatomical Modeling from a 3-D Image and a Surface Mapping," issued Nov. 27, 2012; U.S. Pat. No. 8,190,389, entitled "Adapter for Attaching Electromagnetic Image Guidance Components to a Medical Device," issued May 29, 2012; U.S. Pat. No. 8,123,722, entitled "Devices, Systems and Methods for Treating Disorders of the Ear, Nose and Throat," issued Feb. 28, 2012; U.S. Pat. No. 7,720,521, entitled "Methods and Devices for Performing Procedures within the Ear, Nose, Throat and Paranasal Sinuses," issued May 18, 2010; U.S. Pat. Pub. No. 2014/0364725, entitled "Systems and Methods for Performing Image Guided Procedures within the Ear, Nose, Throat and Paranasal Sinuses," published Dec. 11, 2014; U.S. Pat. Pub. No. 2014/0200444, entitled "Guidewires for Performing Image Guided Procedures," published Jul. 17, 2014; U.S. Pat. No. 9,198,736, entitled "Adapter for Attaching Electromagnetic Image Guidance Components to a Medical Device," issued Dec. 1, 2015; U.S. Pat. Pub. No. 2011/0060214, entitled "Systems and Methods for Performing Image Guided Procedures within the Ear, Nose, Throat and Paranasal Sinuses," published Mar. 10, 2011; U.S. Pat. No. 9,167,961, entitled "Methods and Apparatus for Treating Disorders of the Ear Nose and Throat," issued Oct. 27, 2015; and U.S. Pat. Pub. No. 2007/0208252, entitled "Systems and Methods for Performing Image Guided Procedures within the Ear, Nose, Throat and Paranasal Sinuses," published Sep. 6, 2007, the disclosures of each of the these references being incorporated by reference herein.

II. DEFLECTABLE SHAFT ASSEMBLY AND AXIAL ADJUSTMENT COUPLING FOR A SURGICAL CUTTING INSTRUMENT

While surgical cutting instrument (10) is configured to remove a target tissue as discussed above in greater detail, a particular position of such target tissue within the patient will likely vary, to at least some extent, depending on the patient and the tissue identified for removal. For example, in some instances, the target tissue may be positioned along a relatively linearly extending cavity in the patient or, in other instances, may be positioned along more complex, winding cavities within the patient. In order to access target tissue within such complex, winding cavities, the surgeon may attempt to reposition surgical cutting instrument (10) at one or more awkward angles or even discard surgical cutting instrument (10) for a more suitable instrument depending on the circumstance. Thus, manipulating the position of shaft window opening (50) and cutting window opening (54) for greater access to the target tissue generally provides for greater comfort and enhanced outcomes for the patient.

Figure 3:
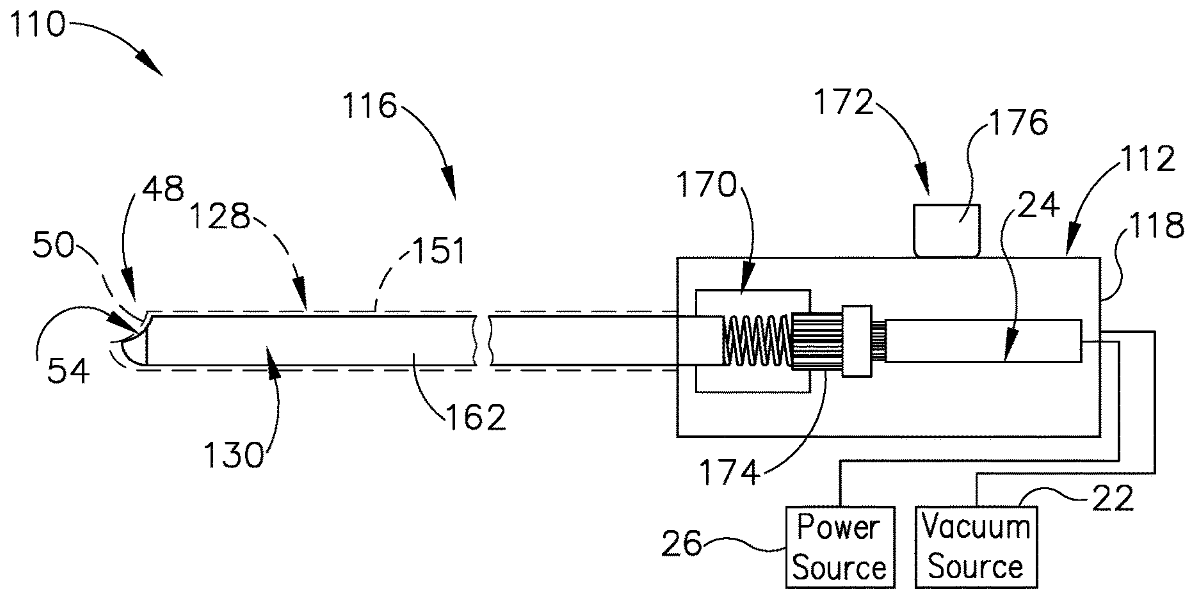
FIG. 3 depicts a schematic side view of a second exemplary surgical cutting instrument having a handle assembly, a deflectable shaft assembly with an articulation mechanism, and an axial adjustment coupling.
Figure 4:
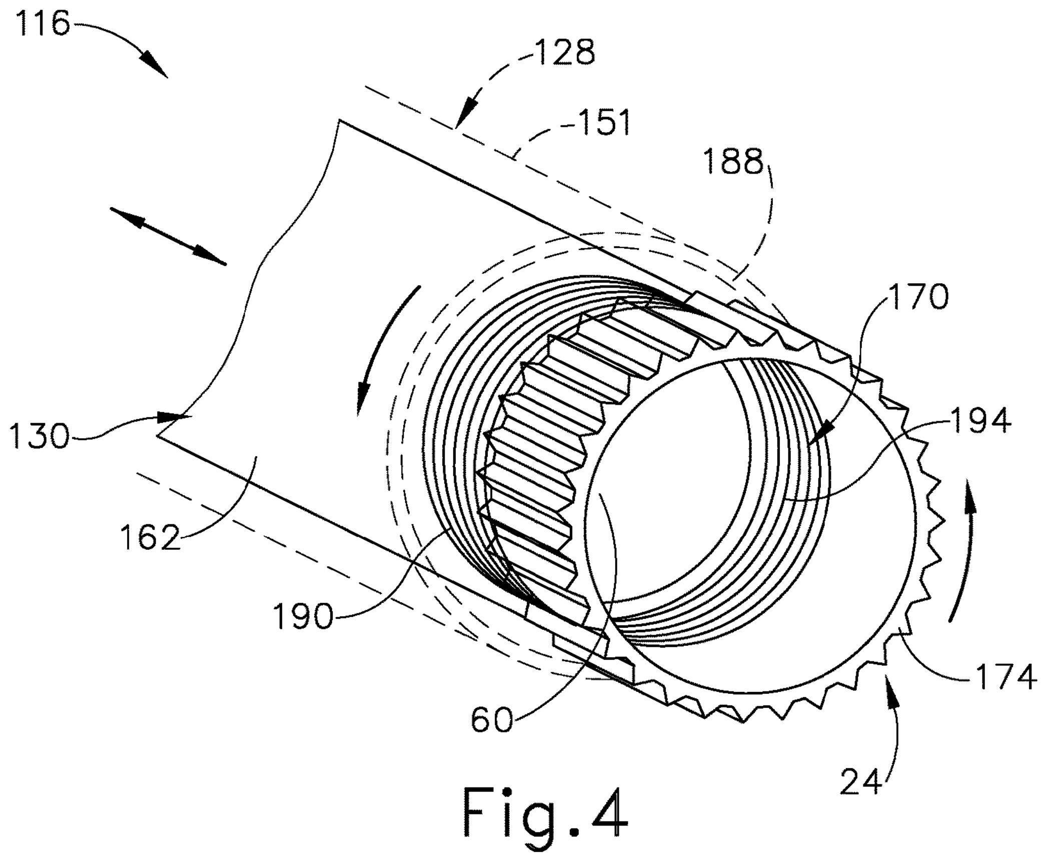
FIG. 4 depicts an enlarged, proximal perspective view of the deflectable shaft assembly and a portion of the axial adjustment coupling of the surgical cutting instrument of FIG. 3.

With respect to FIGS. 3-4, a second exemplary surgical cutting instrument (110) has a deflectable shaft assembly (116) distally extending from a handle assembly (112) and operatively connected thereto via an axial adjustment coupling (170). Surgical cutting instrument (110) further includes an articulation mechanism (172) operatively connected to deflectable shaft assembly (116). Articulation mechanism (172) selectively articulates deflectable shaft assembly (116) between a straight configuration, an upward articulated configuration, and a downward articulated configuration for deflecting distal portions of deflectable shaft assembly (116) relative to proximal portions of deflectable shaft assembly (116) and accessing the target tissue. More particularly, an outer shaft (128) and an inner cutting member (130) of deflectable shaft assembly (116) each respectively articulate along a common longitudinal axis (177) (see FIG. 5A). Such articulation varies the lengths of cutting member (130) and shaft (128) along common longitudinal axis, with the greatest difference being between the straight configuration and the most articulated upward and downward configurations in the present example. Axial adjustment coupling (170) secures cutting member (130) relative to shaft (128) to allow cutting member (130) to longitudinally move along common longitudinal axis (177) (see FIG. 5A) during articulation of deflectable shaft assembly (116) for maintaining alignment between shaft window opening (50) and cutting window opening (54) during use. Various features of surgical cutting instruments (10, 110) may be readily incorporated into each other such that the invention is not intended to be unnecessarily limited to the particular examples shown herein. In any case, like numbers provided below indicate like features discussed above in greater detail.

Handle assembly (112) has a handle body (118) that may include controls for the operation of surgical cutting instrument (110), or the controls may be located remotely. One such control is an activation control (not shown) configured to selectively power motorized drive assembly (24) via power source (26). Vacuum source (22) fluidly connects to suction port (20) (see FIG. 1) to draw a vacuum through suction lumen (60) (see FIG. 4) of cutting member (130) rotatably disposed within shaft (128). Motorized drive assembly (24) rotatably drives cutting member (130) within shaft (128) such that cutting member (130) rotates cyclically and repeatedly through an open state and a closed state in relation to shaft (128). In the open state, cutting window opening (54) aligns with shaft window opening (50) to fluidly communicate the vacuum throughout to the environment for receiving and suctioning tissue therein. In contrast, in the closed state, a tubular sidewall (162) of cutting member (130) aligns with and covers shaft window opening (50) to inhibit further suctioning.

In the present example, shaft (128) is longitudinally and rotationally fixed to handle body (118). Axial adjustment coupling (170) mechanically couples cutting member (130) to a drive output, including a drive output gear (174), such that cutting member (130) rotatably locks to drive output gear (174) while being simultaneously configured to translate relative to drive output gear (174). In turn, cutting member (130) similarly rotates and selectively translates relative to handle body (118) and shaft (128) to accommodate articulation of cutting member (130) relative to articulation of shaft (128) as selectively directed by an articulation input (176) of articulation mechanism (172). While articulation input (176) is shown as a knob in the present example, it will be appreciated that alternative inputs configured to be selectively manipulated by the surgeon may be similarly used.

Figures 5A, 5B, 5C:
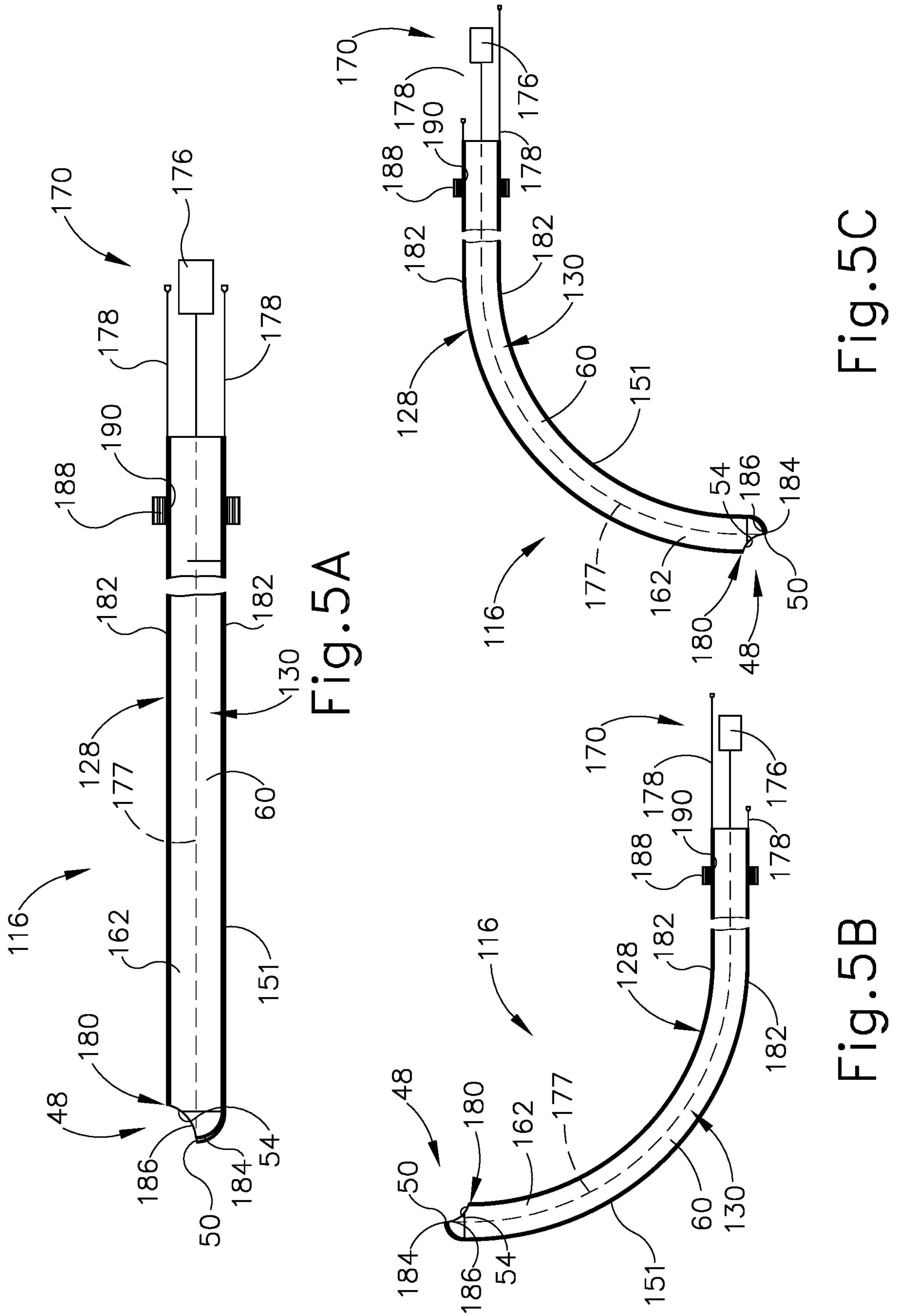
FIG. 5A depicts a schematic, sectional view of the deflectable shaft assembly taken along a centerline thereof with the articulation mechanism of FIG. 3 in a straight configuration.
FIG. 5B depicts the schematic, sectional view of the deflectable shaft assembly similar to FIG. 5A, but showing the shaft assembly with the articulation mechanism in an upward articulated configuration.
FIG. 5C depicts the schematic, sectional view of the deflectable shaft assembly similar to FIG. 5B, but showing the shaft assembly with the articulation mechanism in a downward articulated configuration.

To this end, FIG. 5A shows one example of deflectable shaft assembly (116) in a straight configuration such that common longitudinal axis (177) of shaft (128) and cutting member (130) is generally linear. At least a portion of shaft (128) and at least a portion of cutting member (130) are each formed of one or more flexible materials configured to flexibly deform from this linearly extending common longitudinal axis (177). In addition, at least such portions of cutting member (130) are further configured to transmit sufficient torque during use to cut the target tissue as described above. In one example, cutting member (130) may include an intermediate section having a braided steel material extending from drive output gear (174) (see FIG. 3) to cutting window opening (54) for flexibility therealong. In another example, cutting member (130) may include an intermediate section having a torsional drive cable for similar flexibility. Furthermore, the flexible portion of cutting member (130) in one example may be along an entire longitudinal length of cutting member (130) up to cutting window opening (54) or such flexible portion in another example may be limited to a shorter longitudinal length of cutting member (130) that longitudinally aligns with the flexible portions of shaft (128).

Articulation mechanism (172) includes articulation input (176) connected to a pair of elongate members, such as a pair of cables (178), each connected to a distal end portion (180) of shaft (128). More particularly, cables (178) extend along respective longitudinal channels (182) on angularly opposing sides of a tubular sidewall (151) of shaft (128) about common longitudinal axis (177). Cables (178) are secured to distal end portion (180) of shaft (128) within respective longitudinal channels (182) and proximally extend therefrom into handle body (118) (see FIG. 3) to operatively connect to articulation input (176). In the present example, cables (178) are push-pull cables (178) configured transmit force in tension and compression for more easily articulating deflectable shaft assembly (116). While the present example shows longitudinal channels (182) formed within tubular sidewall (151) of shaft (128), an alternative example may have cables (178) longitudinally extending along an outer surface of tubular sidewall (151) and, in addition, may be positioned in an outer radial groove extending along the outer surface of tubular sidewall (151). An outer sheath (not shown) may further cover cables (178) positioned on the outer surface of shaft (128). Alternatively, rather than dedicated longitudinal channels (182) as discussed above, cables (178) may longitudinally extend in an annular gap between cutting member (130) and shaft (128).

Upon articulation of deflectable shaft assembly (116), a distal shaft end (184) of shaft (128) and a distal member end (186) of cutting member (130) respectively deflect relative to a proximal shaft end (188) of shaft (128) and a proximal member end (190) of cutting member (130). Manipulating articulation input (176) one direction, as shown in FIG. 5B, pulls one cable (178) in tension and pushes the other cable (178) in compression to articulate deflectable shaft assembly (116) from the straight configuration to the upward articulated configuration. More particularly, distal shaft end (184) deflects upward relative to proximal shaft end (188) such that tubular sidewall (151) of shaft (128) similarly urges tubular sidewall (162) of cutting member (130) to follow along the arcuately extending common longitudinal axis (177). Thus, distal member end (186) also deflects upward relative to proximal member end (190) while maintaining longitudinal alignment between shaft window opening (150) and cutting window opening (154) from the straight configuration to the upward articulated configuration.

With respect to FIG. 5C, manipulating articulation input (176) the opposite direction pushes one cable (178) in compression and pulls the other cable (178) in tension to articulate deflectable shaft assembly (116) from the straight configuration to the downward articulated configuration. More particularly, distal shaft end (184) deflects downward relative to proximal shaft end (188) such that tubular sidewall (151) of shaft (128) similarly urges tubular sidewall (162) of cutting member (130) to follow along the arcuately extending common longitudinal axis (177). Thus, distal member end (186) also deflects downward relative to proximal member end (190) while maintaining longitudinal alignment between shaft window opening (150) and cutting window opening (154) from the straight configuration to the downward articulated configuration. While the above description initiates articulation from the straight configuration to each of the upward and downward articulated configurations in the present example, it will be appreciated that such articulation may initiate from any configuration of deflectable shaft assembly (116) and terminate in any configuration of deflectable shaft assembly (116). The invention is thus not intended to be unnecessarily limited to initiate and terminate articulation as shown and described herein. Furthermore, while the present example of deflectable shaft assembly (116) selectively articulates via articulation mechanism (172), an alternative shaft assembly may having one or more portions of cutting member (130) and shaft (128) be formed of a malleable material. Rather than selectively directing articulation input (176), the surgeon may grip and physically manipulate such malleable cutting member and malleable shaft by hand to a desirable shape for use. Thus, the surgeon may manipulate malleable deflectable shaft assembly to at least any articulation as shown in FIGS. 5A-5C.

Figure 6A:
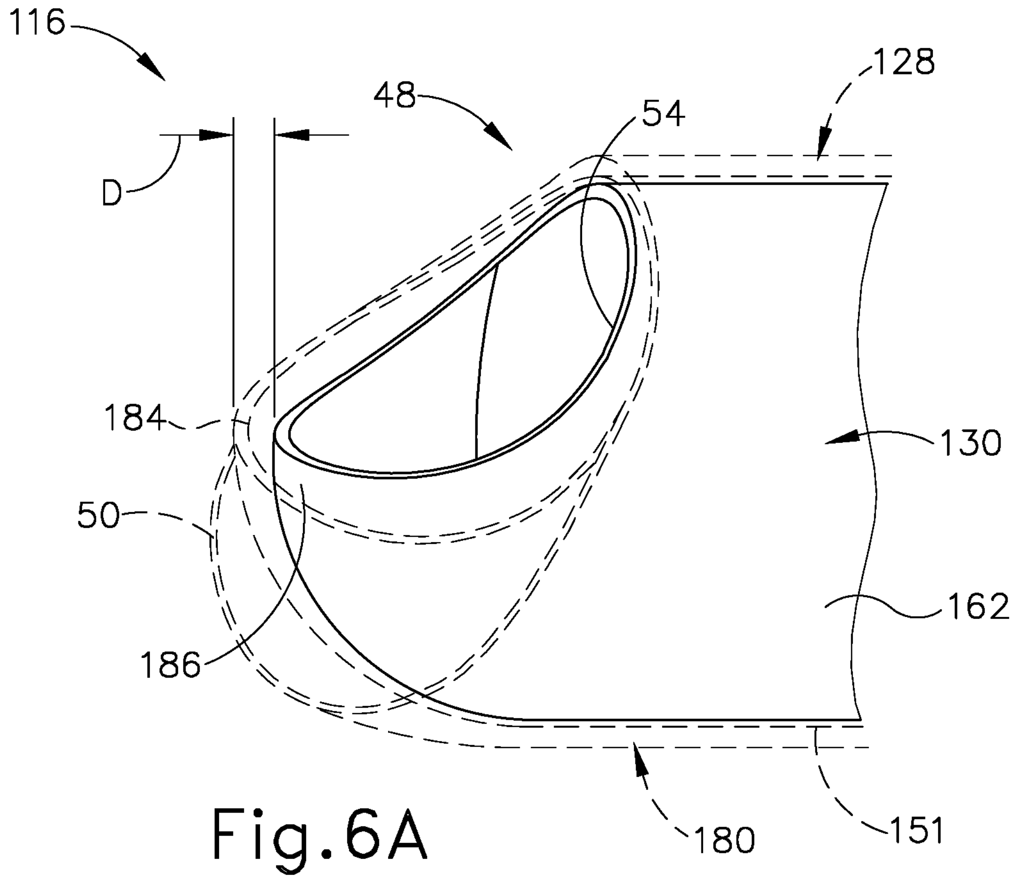
FIG. 6A depicts an enlarged, perspective view of a distal end portion of the deflectable shaft assembly of FIG. 3 in the straight configuration having various features hidden for greater clarity.
Figure 6B:
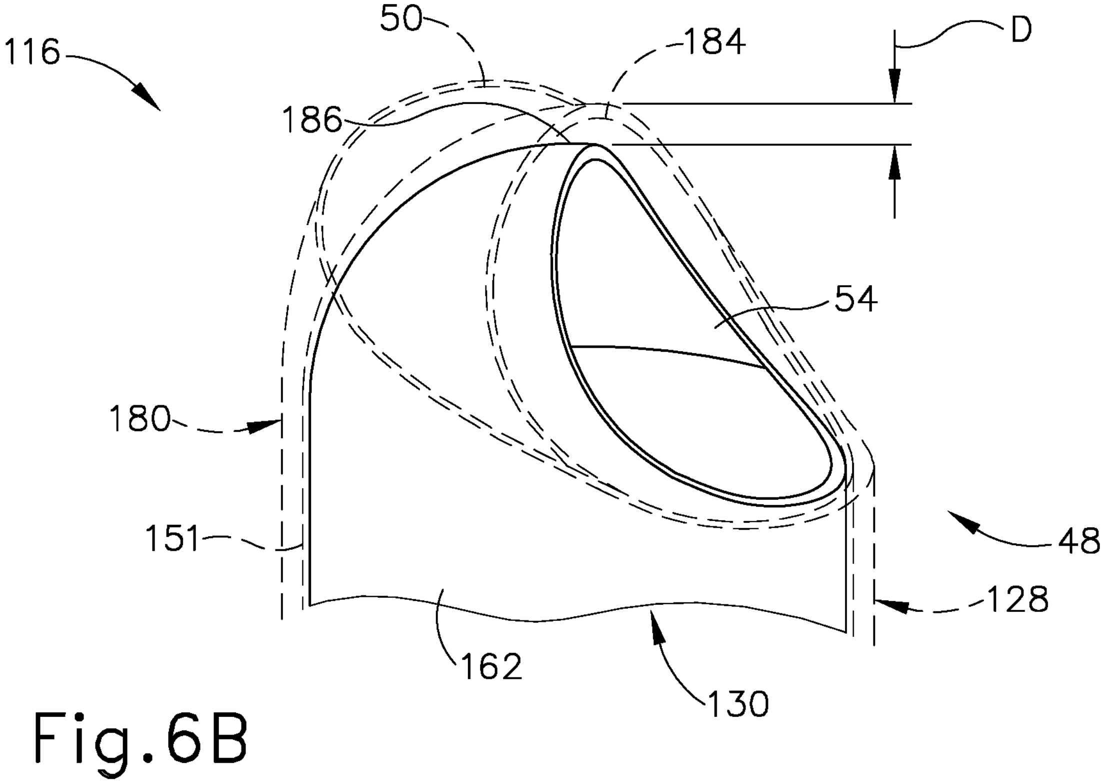
FIG. 6B depicts the enlarged, perspective view of the distal end portion of the deflectable shaft assembly similar to FIG. 6A, but showing the shaft assembly in the upward articulated configuration.

FIGS. 6A-6B show the distal end portion of deflectable shaft assembly (116) in greater detail with distal shaft end (184) of shaft (128) and distal member end (186) of cutting member (130) respectively in the straight and upward articulated configurations. FIG. 6A shows distal member end (186) a predetermined longitudinal distance (D) from distal shaft end (184) in the straight configuration, whereas FIG. 6B shows distal member end (186) the same predetermined longitudinal distance (D) from distal shaft end (184) in the upward articulated configuration. To this end, shaft window opening (150) remains longitudinally aligned with cutting window opening (154) in each of the straight and upward articulated configurations and, indeed, remains similarly aligned in any configuration.

Figure 7A:
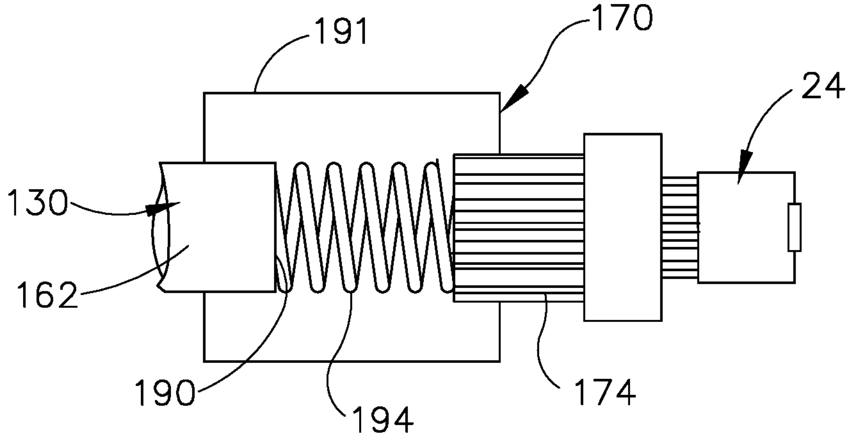
FIG. 7A depicts an enlarged, schematic side view of the axial adjustment coupling connected to a portion of the shaft assembly in the straight configuration of FIG. 6A.
Figure 7B:
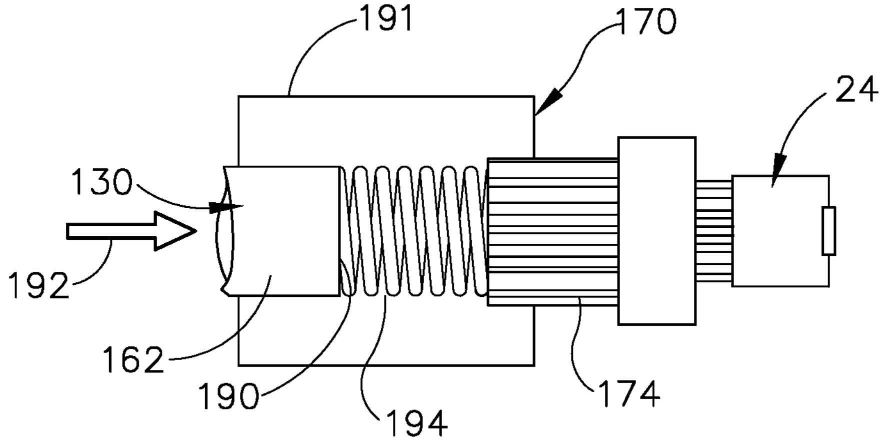
FIG. 7B depicts the enlarged, schematic side view of the axial adjustment coupling connected to a portion of the shaft assembly similar to FIG. 7A, but showing the shaft assembly in the upward articulated configuration of FIG. 6B.

As shown in FIGS. 7A-7B, axial adjustment coupling (170) mechanically couples with cutting member (130) to maintain the predetermined longitudinal distance (D) between distal shaft end (184) and distal member end (186) regardless of the configuration of deflectable shaft assembly (116). In the straight configuration of FIG. 7A, axial adjustment coupling (170) extends between and mechanically couples cutting member (130) to drive output gear (174) of motorized drive assembly (124). More particularly, axial adjustment coupling (170) mechanically locks rotation of drive output gear (174) to proximal member end (190) and transmits torque therethrough such that drive output gear (174) rotatably drives cutting member (130) relative to shaft (128) (see FIG. 3).

While rotatably securing drive output gear (174) to proximal member end (190), axial adjustment coupling (170) has a spline coupling (191) that simultaneously allows for longitudinal translation of proximal member end (190) relative to drive output gear (174) for maintaining the predetermined longitudinal distance (D) (see FIGS. 6A-6B) during articulation. With respect to FIG. 7B, articulating cutting member (130) to the upward articulated configuration causes distal shaft end (184) (see FIG. 6B) to longitudinally engage distal member end (186) and urge cutting member (130) proximally toward drive output gear (174) as indicated by arrow (192). In the present example, proximal member end (190) compresses against a spring (194) such that cutting member (130) is distally biased toward distal shaft end (184). Alternatively or in addition, axial adjustment coupling (170) may include a wave spring assembly and/or bearings to accommodate such longitudinal movement and bias. By way of further example, axial adjustment coupling (170) may include a longitudinal drive mechanism in place of at least spring (194) to actively position cutting member (130) relative to shaft (128). In this respect, the invention is not intended to be unnecessarily limited to passive adjustment, such as by biasing cutting member (130) with spring (194) as shown in the present example. Returning deflectable shaft assembly (116) from the upward biased configuration to the straight configuration will reverse the longitudinal movement of cutting member (130) away from drive output gear (174). Such proximal movement indicated by arrow (192) would similarly occur upon articulating deflectable shaft assembly (116) from the straight configuration to the downward articulated configuration.

Axial adjustment coupling (170) of the present example is connected inline with drive output gear (174) and, indeed, a remainder of motorized drive assembly (124), such that axial adjustment coupling (170) is generally distally positioned relative to drive output gear (174). In another example, axial adjustment coupling (170) may be coaxial with common longitudinal axis (177) (see FIG. 5A) and drive output gear (174) may be positioned on another axis offset from common longitudinal axis (177) (see FIG. 5A). In such an alternative example, one or more portions of axial adjustment coupling (170), such as spring (194), may be proximally positioned relative to drive output gear (174), which is positioned alongside proximal member end (190) of cutting member (130). A driven gear member (not shown) may be coupled to proximal member end (190) to laterally engage drive output gear (174) to drive rotation of cutting member (130). Driven gear member (not shown) would thus remain engaged with drive output gear (174) while longitudinally sliding relative to drive output gear (174) thereby allowing for longitudinal translation of proximal member end (190) relative to drive output gear (174) in order to maintain the predetermined longitudinal distance (D) (see FIGS. 6A-6B) as discussed above.

Figure 8:
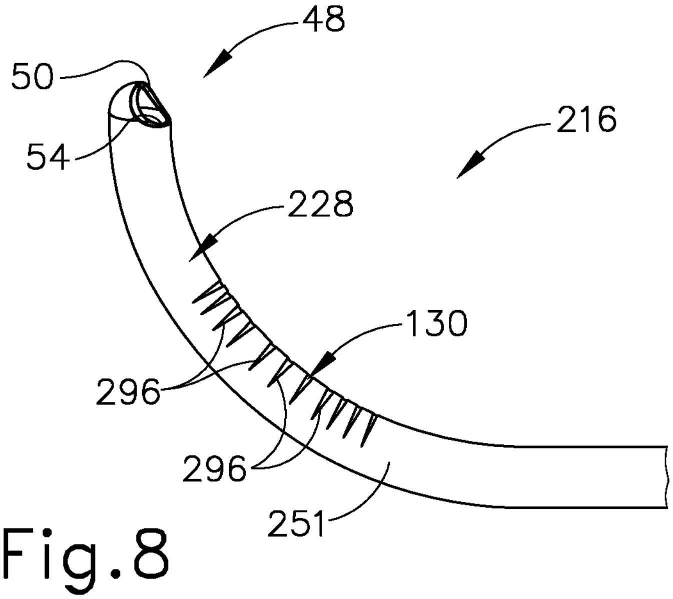
FIG. 8 depicts a perspective view of an alternative deflectable shaft assembly having a plurality of gaps and positioned in an upward articulated configuration.

In another example, FIG. 8 shows an alternative deflectable shaft assembly (216), which has an outer shaft (228) with an inner cutting member (230) similarly configured to deflectable shaft assembly (116) (see FIG. 3) discussed above. However, in addition to or alternatively, shaft (228) has a plurality of gaps (296) positioned longitudinally through tubular sidewall (251) along an inner radius of deflection, such as upward articulated configuration. Gaps (296) are generally opened in the straight configuration and close, to at least some extent, as shaft (228) articulates toward the upward articulated configuration. Gaps (296) provide space for the material of shaft (228) to more easily and predictably deflect during use. Such gaps (296) may be similarly positioned on an opposing side of sidewall (251) to create a similar downward articulated configuration and/or positioned on cutting member (230) for similar deflection thereof. Alternative materials or structures for flexing deflectable shaft assembly (216) may be similarly used, and the invention is not intended to be unnecessarily limited to the flexible materials and structures as shown and described herein.

In order to further aid alignment between an inner, cutting member (130) and an outer shaft, another alternative shaft assembly may include a longitudinally elongated shaft window opening (not shown) configured to remain in communication with cutting window opening (154) as cutting member (130) longitudinally moves within outer shaft. Such elongated shaft window opening (not shown) longitudinally extends further than shaft window opening (50), discussed above, while cutting window opening (154) may remain the same. The additional elongation of elongated shaft window opening (not shown) is sized to accommodate the longitudinal movement of cutting window opening (154) to maintain consistent communication therethrough in any of the configurations shown in FIGS. 5A-5C.

In use, with respect to FIGS. 3-5C, surgeon introduces the distal end portion of deflectable shaft assembly (216) into the nasal cavity of the patient toward the target tissue while the deflectable shaft assembly (216) is in the straight configuration. The surgeon manipulates the articulation input (176) to articulate deflectable shaft assembly (216) from the straight configuration toward either the upward or downward articulated configurations as desired for accessing the target tissue with the shaft and cutting window openings (50, 54). During the articulation shown in FIGS. 5A-5C, cables (178) push and pull on distal end portion (180) of shaft (128) such that shaft (128) urges cutting member (130) along common longitudinal axis (177) to collectively articulate deflectable shaft assembly (116).

With respect to FIGS. 6A-7B, distal shaft end (184) engages distal member end (186) and proximally translates cutting member (130) to urge proximal member end (190) relative to proximal shaft end (188) (see FIG. 3) and toward drive output gear (174). Axial adjustment coupling (170) biases distal member end (186) toward distal shaft end (184), but spring (194) resiliently compresses to accommodate the longitudinal translation of cutting member (130), while spline coupling (191) simultaneously remains rotatably locked to cutting member (130). The translation of proximal member end (190) thereby retains the predetermined longitudinal distance (D) between distal shaft end (184) and distal member end (186) to maintain longitudinal alignment of shaft and cutting window openings (50, 54) regardless of the particular configuration of deflectable shaft assembly (116).

Once shaft window opening (50) accesses the target tissue, the surgeon selectively powers motorized drive assembly (124) to transmit torque from drive output gear (174) and through axial adjustment coupling (170) to rotatably drive cutting member (130) to cut and remove the target tissue against cutting edge (58) (see FIG. 2) as discussed above. While the above description first articulates deflectable shaft assembly (116) and then rotatably drives cutting member (130) to cut the target tissue, the surgeon may alternatively drive cutting member (130) while simultaneously articulating deflectable shaft assembly (116) in other examples.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft configured to articulate from a first configuration toward a first articulated configuration, including: (i) a distal shaft end, (ii) a proximal shaft end, (iii) a shaft sidewall extending from the distal shaft end to the proximal shaft end and configured to move the distal shaft end relative to the proximal shaft, and (iv) a shaft window opening extending through the shaft sidewall; (b) a cutting member disposed within the shaft and configured to cyclically move relative to the shaft, wherein the cutting member is further configured to articulate within the shaft from the first configuration toward the second configuration, including: (i) a distal member end, (ii) a proximal member end, (iii) a member sidewall extending from the distal member end to the proximal member end and configured to move the distal member end relative to the proximal member end, (iv) a cutting window opening extending through the member sidewall and configured to align with the shaft window during cyclical movement relative thereto and receive a tissue for cutting, and (c) an axial adjustment coupling longitudinally securing the shaft relative to the cutting member and configured to longitudinally move the proximal member end relative to the proximal shaft end while articulating the shaft and the cutting member from the first configuration toward the second configuration to inhibit movement of the distal member end relative to the distal shaft end for maintaining alignment between the shaft window opening and the cutting window opening.

Example 2

The surgical instrument of Example 1, wherein the cutting member further includes a suction lumen extending longitudinally therethrough and in fluid communication with the cutting window opening, wherein the cutting window opening is configured to align with the shaft opening during cyclical movement relative thereto such that the cutting window opening and the shaft opening are in fluid communication for suctioning the tissue therethrough.

Example 3

The surgical instrument of any one or more of Examples 1 through 2, wherein the axial adjustment coupling longitudinally biases the distal member end toward the distal shaft end.

Example 4

The surgical instrument of any one or more of Examples 1 through 3, further comprising at least a portion of a motorized drive assembly, wherein the axial adjustment coupling rotatably secures the cutting member relative to the at least the portion of the motorized drive assembly to inhibit relative rotation therebetween.

Example 5

The surgical instrument of any one or more of Examples 1 through 4, wherein the shaft is configured to articulate from the first configuration toward a third configuration, and wherein the cutting member is further configured to articulate within the shaft from the first configuration toward the third configuration.

Example 6

The surgical instrument of Example 5, wherein the first configuration is a first straight configuration, wherein the second configuration is a first articulated configuration, and wherein the third configuration is a second articulated configuration, and wherein the second articulated configuration is bent opposite from the first articulated configuration.

Example 7

The surgical instrument of any one or more of Examples 1 through 6, further comprising an articulation mechanism operatively connected to the shaft and the cutting member and configured to articulate the shaft and the cutting member from the first configuration toward the second configuration.

Example 8

The surgical instrument of Example 7, wherein the articulation mechanism includes an elongate member connected to the shaft, and wherein the elongate member is configured to be pulled and thereby articulate the shaft from the first configuration toward the second configuration.

Example 9

The surgical instrument of Example 8, wherein the shaft sidewall is configured to engage the member sidewall while moving from the first configuration toward the second configuration to urge the cutting member from the first configuration toward the second configuration.

Example 10

The surgical instrument of Example 8, further comprising a body assembly having the shaft and the cutting member distally extending therefrom, wherein the articulation mechanism further includes an articulation input positioned on the body assembly and operatively connected to the elongate member, wherein the articulation input is configured to selectively urge the elongate member to direct the shaft from the first configuration toward the second configuration.

Example 11

The surgical instrument of any one or more of Examples 1 through 10, wherein at least a portion of the shaft configured to articulate is formed from a flexible material.

Example 12

The surgical instrument of any one or more of Examples 1 through 11, wherein at least a portion of the shaft configured to articulate has a plurality of gaps positioned longitudinally therealong, wherein the plurality of gaps are respectively configured to at least partially close together in the second configuration.

Example 13

The surgical instrument of any one or more of Examples 1 through 12, further comprising a body assembly including a motorized drive assembly, wherein the shaft and the cutting member distally extend from the body assembly.

Example 14

The surgical instrument of Example 13, wherein the motorized drive assembly includes a drive output member, and wherein the axial adjustment coupling rotatably secures the cutting member relative to the drive output member to inhibit relative rotation therebetween.

Example 15

The surgical instrument of any one or more of Examples 1 through 14, wherein the shaft is a shaft tube and the cutting member is a cutting member tube.

Example 16

A surgical instrument, comprising: (a) a body assembly including a motorized drive assembly having a drive output member; (b) a shaft distally extending from the body assembly and configured to articulate from a straight configuration toward an articulated configuration, including: (i) a distal shaft end, (ii) a proximal shaft end, (iii) a shaft sidewall extending from the distal shaft end to the proximal shaft end and configured to move the distal shaft end relative to the proximal shaft, and (iv) a shaft window opening extending through the shaft sidewall; (c) a cutting member disposed within the shaft and configured to cyclically move relative to the shaft, wherein the cutting member is further configured to articulate within the shaft from the straight configuration toward the articulated configuration, including: (i) a distal member end, (ii) a proximal member end, (iii) a member sidewall extending from the distal member end to the proximal member end and configured to move the distal member end relative to the proximal member end, (iv) a cutting window opening extending through the member sidewall and configured to align with the shaft window during cyclical movement relative thereto and receive a tissue for cutting, and (d) an axial adjustment coupling longitudinally securing the shaft relative to the cutting member and rotatably securing the cutting member relative to the drive output member, wherein the axial adjustment coupling biases the distal member end toward the distal shaft end and is configured to longitudinally move the proximal member end relative to the proximal shaft end while articulating the shaft and the cutting member from the straight configuration toward the articulated configuration to inhibit movement of the distal member end relative to the distal shaft end for maintaining alignment between the shaft window opening and the cutting window opening.

Example 17

The surgical instrument of Example 16, further comprising an articulation mechanism having an elongate member connected to the shaft, and wherein the elongate member is configured to be pulled and thereby articulate the shaft from the straight configuration toward the articulated configuration.

Example 18

A method of accessing a tissue with a surgical instrument, wherein the surgical instrument includes a shaft extending from a distal shaft end to a proximal shaft end and a cutting member extending from a distal member end to a proximal member end, the cutting member disposed within the shaft and configured to cyclically move relative to the shaft, wherein the shaft and the cutting member are configured to articulate from a straight configuration toward an articulated configuration, the method comprising: (a) articulating the shaft and the cutting member from the straight configuration toward the articulated configuration; (b) longitudinally moving the proximal member end relative to the proximal shaft end with an axial adjustment coupling thereby maintaining a longitudinal position of the distal member end relative to the distal shaft end throughout articulation from the straight configuration toward the articulated configuration; and (c) accessing the tissue with the shaft and the cutting member in the articulated configuration.

Example 19

The method of Example 18, further comprising biasing the distal member end of the cutting member toward the distal shaft end of the shaft.

Example 20

The method of any one or more of Examples 18 through 19, further comprising rotating the cutting member relative to the shaft within the shaft while inhibiting rotation of the cutting member relative to a drive output member of a motorized drive assembly with the axial adjustment coupling connected therebetween.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using a surgical instrument to treat a tissue within a nasal cavity of a patient, the surgical instrument including:
- a shaft having:
  - a distal shaft end,
  - a proximal shaft end,
  - a shaft sidewall extending from the distal shaft end to the proximal shaft end relative to the proximal shaft end, and
  - a shaft window opening extending through the shaft sidewall;
- a cutting member rotatably disposed within the shaft and having:
  - a distal member end,
  - a proximal member end,
  - a member sidewall extending from the distal member end to the proximal member end, and
  - a cutting window opening extending through the member sidewall; and
- an axial adjustment coupling that coupled to the proximal member end of the cutting member and securing the cutting member relative to the shaft to allow cutting member to longitudinally move along a longitudinal axis thereof for maintaining alignment between the shaft window opening and the cutting window opening during use, the axial adjustment coupling having a spline coupling that includes a spring, the spline coupling simultaneously transferring torque and allowing for longitudinal translation of the proximal member end relative to a drive output gear for maintaining a predetermined longitudinal distance between the distal member end and the distal shaft end;

the method comprising:
- (a) articulating the shaft and the cutting member from a first configuration towards a second configuration during an active medical procedure;
- (b) moving the cutting member with a cyclical movement; and
- (c) maintaining the predetermined longitudinal distance distance between the distal member end and the distal shaft end before, during, and after the step of articulating.

2. The method of claim 1, further comprising inserting the surgical instrument into the nasal cavity.

3. The method of claim 2, the axial adjustment coupling being proximally located relative to the proximal member end.

4. The method of claim 3, the axial adjustment coupling including a resilient member.

5. The method of claim 4, the resilient member including a spring.

6. The method of claim 5, further comprising biasing the distal member end towards the distal shaft end and compressing the spring to allow the distal member end to move in a proximal direction relative to the proximal shaft end to perform the act of maintaining the predetermined longitudinal distance between the distal member end and the distal shaft end.

7. The method of claim 1, further comprising engaging the tissue.

8. The method of claim 7, further comprising severing the tissue from the nasal cavity.

9. The method of claim 8, further comprising applying suction to a lumen positioned within the cutting member to remove the tissue from the nasal cavity.

10. The method of claim 9, further comprising tracking a location of the surgical instrument with a navigation system.

11. The method of claim 1, the act of moving the cutting member with the cyclical movement comprising rotating the cutting member.

12. The method of claim 1, the shaft having a proximal shaft portion defining a longitudinal axis and a distal shaft portion extending distally from the proximal shaft portion, the first configuration the distal shaft portion being aligned with the longitudinal axis, and the second configuration the distal shaft portion being angularly positioned relative to the longitudinal axis.

13. The method of claim 12, the second configuration including a first articulated configuration and a second articulated configuration, the distal shaft portion being angularly positioned on a first side of the longitudinal axis in the first articulated configuration, the distal shaft portion being angularly positioned on a second side of the longitudinal axis that is opposite the first side of the longitudinal axis in the second articulated configuration.

14. The method of claim 1, further comprising transmitting force in tension and compression with a pair of push-pull cables to perform the act of articulating the shaft and the cutting member from the first configuration towards the second configuration.

15. A method of using a surgical instrument to treat a tissue within a nasal cavity of a patient, the surgical instrument including:

(a) a shaft having:
  (i) a distal shaft end,
  (ii) a proximal shaft end,
  (iii) a shaft sidewall extending from the distal shaft end to the proximal shaft end relative to the proximal shaft end, and
  (iv) a shaft window opening extending through the shaft sidewall;
(b) a cutting member disposed within the shaft and having:
  (i) a distal member end,
  (ii) a proximal member end,
  (iii) a member sidewall extending from the distal member end to the proximal member end, and
  (iv) a cutting window opening extending through the member sidewall; and
(c) an axial adjustment coupling coupled to the proximal member end of the cutting member and longitudinally securing the shaft relative to the cutting member to allow the cutting member to longitudinally move along a longitudinal axis thereof for maintaining alignment between the shaft window opening and the cutting window opening during use, the axial adjustment coupling having a spline coupling that includes a spring, the spline coupling simultaneously transferring torque and allowing for longitudinal translation of the proximal member end relative to a drive output gear for maintaining a predetermined longitudinal distance between the distal member end and the distal shaft end;

the method comprising:

(a) articulating the shaft and the cutting member from a first configuration towards a second configuration during an active medical procedure; and
(b) biasing the distal member end towards the distal shaft end, thereby maintaining the predetermined longitudinal distance between the distal member end and the distal shaft end before, during, and after the step of articulating.

16. The method of claim 15, the axial adjustment coupling comprising a spring positioned proximal of the proximal shaft end.

17. The method of claim 16, further comprising longitudinally compressing the spring to perform the act of maintaining the predetermined distance between the distal member end and the distal shaft end while simultaneously articulating the shaft and the cutting member from the first configuration towards the second configuration.

18. The method of claim 17, the act of maintaining the predetermined distance between the distal member end and the distal shaft end including non-contact of the distal member end with a proximal surface of the distal shaft end.

19. A method of using a surgical instrument to treat a tissue within a nasal cavity of a patient, the surgical instrument including:

(a) a shaft having:
  (i) a distal shaft end,
  (ii) a proximal shaft end,
  (iii) a shaft sidewall extending from the distal shaft end to the proximal shaft end relative to the proximal shaft end, and
  (iv) a shaft window opening extending through the shaft sidewall;
(b) a cutting member disposed within the shaft and having:
  (i) a distal member end,
  (ii) a proximal member end,
  (iii) a member sidewall extending from the distal member end to the proximal member end, and
  (iv) a cutting window opening extending through the member sidewall; and
(c) an axial adjustment coupling coupled to the proximal member end of the cutting member and longitudinally securing the shaft relative to the cutting member to allow the cutting member to longitudinally move along a longitudinal axis thereof for maintaining alignment between the shaft window opening and the cutting window opening during use, the axial adjustment coupling having a spline coupling that includes a spring, the spline coupling simultaneously transferring torque and allowing for longitudinal translation of the proximal member end relative to a drive output gear for maintaining a predetermined longitudinal distance between the distal member end and the distal shaft end, the method comprising:

(a) articulating the shaft and the cutting member from a straight configuration towards an articulated configuration during an active medical procedure; and
(b) biasing the distal member end towards the distal shaft end, thereby maintaining a gap defined by the predetermined longitudinal distance between the distal member end and the distal shaft end while articulating the shaft and the cutting member.

20. The method of claim 19, further comprising maintaining an alignment of the cutting window opening with the shaft window opening simultaneously while performing the act of articulating the shaft and the cutting member from the straight configuration towards the articulated configuration.

* * * * *